United States Patent
Kerschbaumer et al.

(10) Patent No.: US 7,106,958 B2
(45) Date of Patent: Sep. 12, 2006

(54) INTRA-ORAL CAMERA AND A METHOD FOR USING SAME

(75) Inventors: Harald Kerschbaumer, Klaus (AT); Gottfried Rohner, Altstatten (CH); Walter Pokorny, Thuringen (AT)

(73) Assignee: Ivoclar Vivadent AG, Schaan (LI)

( * ) Notice: Subject to any disclaimer, the term of this patent is extended or adjusted under 35 U.S.C. 154(b) by 103 days.

(21) Appl. No.: 10/820,579

(22) Filed: Apr. 8, 2004

(65) Prior Publication Data

US 2005/0100333 A1 May 12, 2005

(30) Foreign Application Priority Data

Nov. 10, 2003 (DE) .............. P 103 52 394

(51) Int. Cl.
  *A61B 1/24* (2006.01)
  *G03B 7/02* (2006.01)
(52) U.S. Cl. .................... 396/16; 396/281; 348/66; 348/77
(58) Field of Classification Search .......... 396/16, 396/263, 157, 201, 202, 281; 348/66, 77
See application file for complete search history.

(56) References Cited

U.S. PATENT DOCUMENTS

| | | | |
|---|---|---|---|
| 4,184,175 A * | 1/1980 | Mullane, Jr. ............... | 348/66 |
| 4,268,154 A * | 5/1981 | Daitoku ..................... | 396/264 |
| 5,051,823 A * | 9/1991 | Cooper et al. ............. | 348/66 |
| 5,270,765 A * | 12/1993 | Kunishige .................. | 396/123 |
| 6,201,880 B1 * | 3/2001 | Elbaum et al. ............ | 382/100 |
| 6,210,159 B1 | 4/2001 | Lehmann et al. | |
| 6,305,933 B1 | 10/2001 | Lehmann | |
| 6,606,458 B1 * | 8/2003 | Umeda et al. ............. | 396/110 |
| 6,885,464 B1 * | 4/2005 | Pfeiffer et al. ............ | 356/602 |
| 2002/0150015 A1 * | 10/2002 | Matos ....................... | 369/53.1 |
| 2003/0148243 A1 * | 8/2003 | Kerschbaumer et al. ..... | 433/29 |

FOREIGN PATENT DOCUMENTS

| | | |
|---|---|---|
| DE | 198 29 278 C1 | 2/2000 |
| DE | 100 43 749 A1 | 3/2002 |
| DE | 10120717 A1 | 10/2002 |
| DE | 10126997 A1 | 12/2002 |
| WO | WO 00/25696 A1 | 5/2000 |

* cited by examiner

*Primary Examiner*—W. B. Perkey
*Assistant Examiner*—Rishi Suthar
(74) *Attorney, Agent, or Firm*—John C. Thompson; Alan S. Korman

(57) ABSTRACT

An intra-oral camera for producing an axially aligned picture of an intra-oral item of interest permits a rapid taking of pictures, whereby burdensome usage requirements are avoided without, however, suffering any diminishment in the quality of the picture that is taken. A computer-controlled picture taking positioning of the intra-oral camera properly positions the camera for taking pictures of objects of interest. The proper picture taking position of the camera ensures that the picture of an intra-oral object or an area of interest such as, for example, a tooth of a patient, is taken in the desired size, at the desired angle, and at the desired location.

3 Claims, 10 Drawing Sheets

INTRA-ORAL CAMERA AND A METHOD FOR USING SAME

CROSS-REFERENCE TO RELATED APPLICATIONS

This application claims foreign priority benefits under 35 U.S.C. §119 from German patent application Ser. No. 103 52 394.4 filed Nov. 10, 2003.

TECHNICAL FIELD

The present invention relates to an intra-oral camera as well as a method for using such an intra-oral camera.

BACKGROUND OF THE INVENTION

The use of intra-oral video and/or picture taking-systems (hereinafter designated as an "intra-oral camera system" and as a camera device), has strongly increased over the recent years in the area of use of dental medicine. Such systems are deployed in a variety of settings as well as in situations in which a dentist desires to point out and display certain features of a patient's mouth. These intra-oral camera systems are more and more frequently the passport to complex diagnostic and treatment planning. With respect to such systems, it has been shown that approximately 30% of the practicing dentists between ages 35 and 54 own intra-oral camera systems and use such. It is expected that this percentage will increase as confidence is gained in the use of such systems, according to Dental Procedures Report, pages 22 to 24, February 1995.

Intra-oral camera systems are often deployed in connection with dental restoration efforts. Many people opt nowadays for clinical intervention to improve, via restorative processes, their smiles and appearance. In most such processes, modification of the form or shape of the tooth, the position of the tooth, and/or the color of the tooth are involved.

A necessary step in connection with the modification of the color of a tooth of a patient is the determination of the color shade of the respective tooth. In this connection, for example, the color of the teeth of those patients who are interested in a whiter, beaming smile are evaluated so that a comparison between the appearance of the teeth prior to the restorative treatment and the appearance of the teeth after the restorative treatment can be undertaken. The determination of the color shade is even more important for those persons who require replacement teeth; it is the goal of such restoration processes to achieve a natural appearance of the replacement teeth. For this reason, it is important to properly identify the color shade of the respective tooth so that the new restoration piece can be approximated to the original tooth or teeth.

Typically, a picture of a tooth is taken and a color shade analysis system is used in order to receive suitable information concerning the color shade and the tooth form. The users of such systems often find it difficult to properly orient the intra-oral camera. A correct axial orientation and proper picture taking alignment is, however, of significant importance for enabling the use of analysis software which then processes the picture of the tooth to determine the color shade of the respective tooth.

The size of the region of interest, the size of the camera, the intra-oral location of the area of interest, and, as well, other factors, render difficult the relevant analysis, as such factors influence the two-dimensional picture that is taken. In this connection, it may occur that less than desirable pictures are taken, such as pictures in which a to-be highlighted area of the respective tooth has been cut out or pictures of teeth that are not of interest.

A further disadvantage of such systems, which involve picture taking via a hand-held camera, is that even relatively small hand movements (such as, for example, the movement of a finger to press the shutter actuator) can cause a considerable deviation of the camera from its proper picture taking orientation.

Frequently, the taking of a satisfactory picture of an intra-oral item of interest requires, in connection with such known conventional systems, repeated attempts and/or the burdensome deployment of various devices.

OBJECTS AND SUMMARY OF THE INVENTION

The present invention offers a solution to the challenge of providing an intra-oral camera as well as a method of using such an intra-oral camera for producing an axially aligned picture of an intra-oral item of interest which permits a rapid taking of picture, whereby burdensome usage requirements are avoided without, however, suffering any diminishment in the quality of the picture that is taken.

In accordance with the present invention, a computer controlled picture taking positioning of the intra-oral camera properly positions the camera for taking pictures of objects of interest. The proper picture taking position of the camera ensures that the picture of an intra-oral object or an area of interest such as, for example, a tooth of a patient, is taken in the desired size, at the desired angle, and at the desired location. Drawing upon experience, one can set or adjust beforehand all relevant picture taking parameters so that an error-causing hand movement is foreclosed. The devices for setting the proper picture taking position can use a light source emitting a substantially pinpoint light which is oriented toward the respective object of interest that just then, at that instance, is viewable via the viewfinder of the camera or that is oriented toward the camera. In connection with pinpoint light sources, a laser diode or another light source can be deployed which produces a point of light or a limited light beam region. The pinpoint light source can also be integrated into the camera.

In connection with pinpoint-type light sources, it is to be understood that this concept does not relate to the form of the light source itself but, rather, to the type of light emitted by the light source and directed as a light beam onto an area to be illuminated. This light beam is preferably a pinpoint light beam—that is, the light beam is substantially annular—whereupon a light beam of this type can also be characterized as a point of light or as a light patch.

The light emitted from a pinpoint light source, which is, in turn, reflected by an object of interest, is evaluated, in accordance with the present invention, so as to verify whether a camera is directly oriented toward a respective location a picture of which is desired. A selectively cropped camera frame portion is used to evaluate the orientation of the camera. The selectively cropped camera frame portion can be selected such that it is suitable in shape and size relative to the respective point of light that is produced by the irradiation of the relevant object or area of interest by the pinpoint light source. The distance between the camera and its target is preferably a predetermined distance or spacing which can be set or adjusted via the use of a short standoff tube or a standoff retainer.

In accordance with one embodiment of the present invention, the user can be provided with information which specifies the distances at which the pictures should be taken.

In accordance with the present invention, it is provided that a geometric pattern such as a grating, raster points, an intensity distribution or the like—that is, a two-dimensional reference system—is imposed or overlaid on the picture in order to determine the size of the angle deviation in connection with the orientation of the camera and, at the same time, to provide information for undertaking a correction of the angle deviation. The correction can be effected via a corresponding signal to effect "trimming" in the relevant direction. It is also possible to emit an optical or acoustic signal that indicates that the camera is now exactly aligned or on target.

In an embodiment of the present invention, it is provided that actuation of the shutter actuator for the camera can only be undertaken if a picture target alignment has been performed. It is also possible to use the picture target alignment as a type of trigger signal for actuation of the camera so that the taking of the picture upon pressing of the camera shutter actuator can only be effected if the picture target alignment has been performed.

With regard to the concept of a point of light, it is to be understood that this concept has reference to a limited lighted or illuminated region. Typically, a light patch created by light emitted from a pinpoint light source has an annular shape or configuration, wherein the highest intensity thereof is in the central portion of the light patch. A light region or light patch of this type is herein designated as a point of light.

The selectively cropped camera frame portion, which is used for evaluating the camera orientation, is, in an advantageous embodiment of the present invention, used in connection with evaluating sub-areas into which the selectively cropped frame portion has been subdivided or partitioned, such sub-areas being herein designated as "subdivisions." The content of the subdivisions (for example, their light properties) can be evaluated in order to verify whether the camera is substantially in proper picture taking alignment with respect to the respective area to be photographed. In this connection, two or more subdivisions are compared with one another. The subdivisions can, for example, be grating fields comprised of the previously noted gratings. It is also possible to establish a gradation of the intensity values of the light intensities among the subdivisions.

The devices for setting the proper picture taking position can, for example, have targeting software associated therewith to generate an indication that the camera is substantially in proper picture taking alignment with the respective area to be photographed, wherein the confirmation of such alignment is based upon information concerning the light produced by the pinpoint light source. The indication can be an audible or visible indication. For example, a green light can illuminate in a designated area of a display of a camera to indicate a proper picture taking alignment. Correspondingly, a picture of the instantaneous camera view can be taken and automatically or manually stored. In the event that such is desired, a system of this type can be so configured to permit the user to chose an automatic picture taking mode in which the camera will take a picture automatically.

In an advantageous embodiment of the present invention, the intra-oral camera is automated in order to deliver a fast, precise, and reliable picture of an intra-oral object of interest. A pinpoint light source such as, for example, a laser diode, serves to verify when a camera in an intra-oral camera system has assumed the desired position for the taking of a picture.

The intra-oral camera system automatically takes the picture without requiring user intervention, provided that certain criteria are fulfilled. In this connection, the picture is subdivided into selectively cropped camera frame portions each of which is evaluated. The selectively cropped camera frame portions are of a form which is suitable for the point of light, produced by the pinpoint light source, that irradiates the object to be photographed. The selectively cropped camera frame portion is preferably subdivided into subdivisions which can be used for a comparison analysis, whereby the properly aligned orientation of the intra-oral camera can be verified.

Further details, advantages, and features of the present invention are described in the hereinafter-following description of an embodiment of the present invention taken with reference to the figures of the drawings.

DETAILED DESCRIPTION

Figure 1:
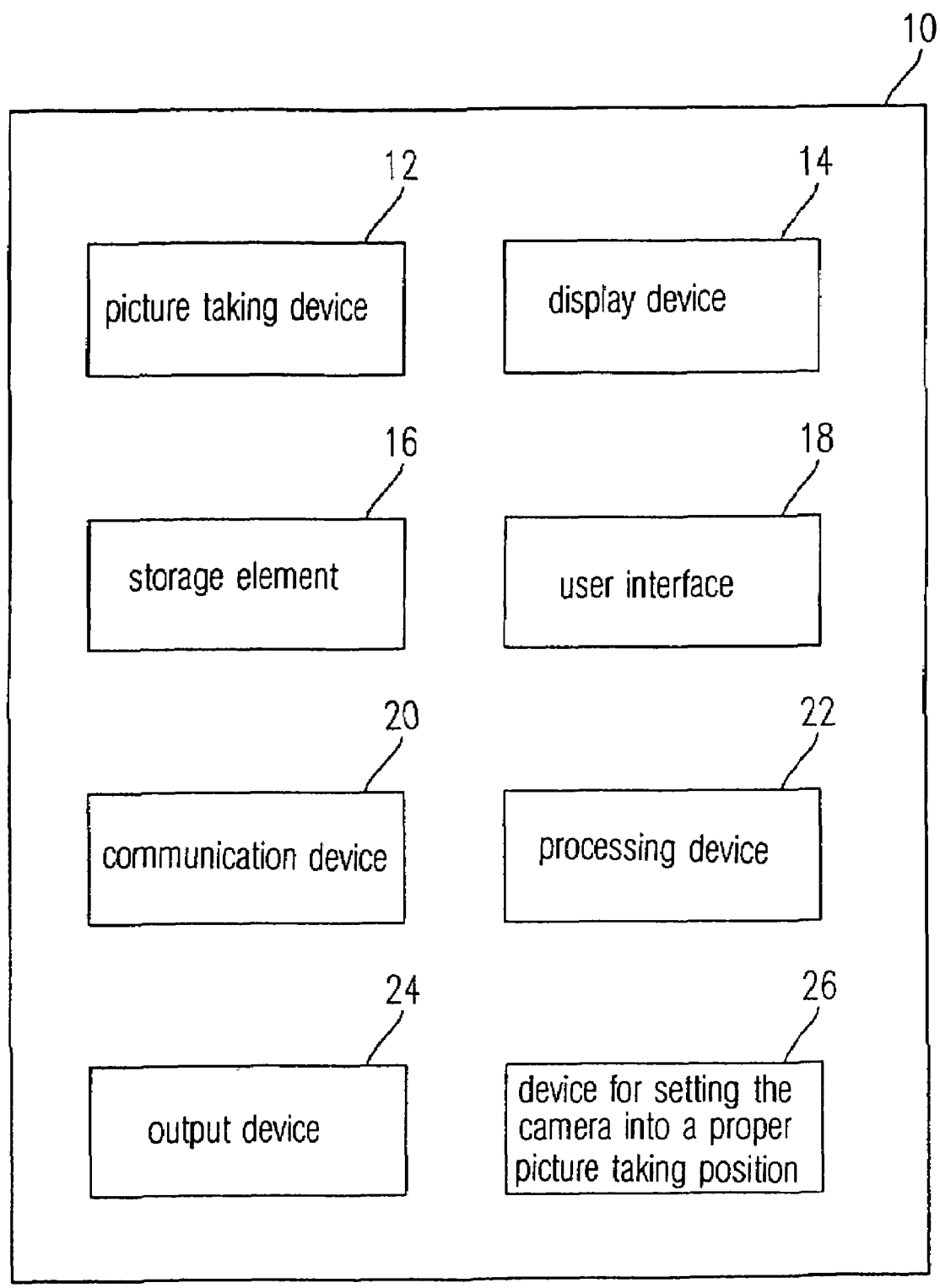
FIG. 1 is a functional block diagram of one embodiment of the intra-oral camera device of the present invention, whereby the camera device is hereinafter also referred to as a camera system.

FIG. 1 shows a functional block diagram of an embodiment of the intra-oral camera system of the present invention. FIG. 1 shows an intra-oral camera system 10 which is used for obtaining picture information of a tooth of a patient. The intra-oral camera system 10 can be deployed, in particular, to produce metrics concerning the color or shape properties of a tooth. In this connection, the respective color shade of a tooth to be observed can be characterized and other desired capturable information can also be obtained. In the illustrated embodiment, the intra-oral camera system 10 comprises a picture taking device 12, a display device 14, a memory 16, a user interface 18, a communications device 20, a processing device 22, and a device for setting the camera into a proper picture taking position 26.

The picture taking device 12 is a device for obtaining information concerning physical and/or color-related properties of a tooth of a patient. The picture taking device comprises a digital camera (for example, an intra-oral camera). Examples of suitable picture taking devices include the camera Power 0/00, which is manufactured by the Insight Company in San Carlos, Calif., and the Cygenascope brand camera manufactured by Cygnus Instruments, Inc. in Goleta, Calif. A further example of such a camera is the model VistaCam. Such cameras are the type of cameras which can be freely supported in the hand of a user. The cameras typically comprise a display, a storage component, software, and a port for communicate with a personal computer. Such cameras are in the position to capture the light characteristics, the color, the color shade, the type of color, or, as well, the color saturation of the object of interest and to take a picture while taking into consideration such factors. The color can be classified in any suitable desired classification code such as, for example, classified in accordance with RGB, in accordance with L*, a*, b*, or in another suitable desired classified manner.

In another embodiment of the present invention, it is provided that additional properties of the picture or, as well, of the selectively cropped camera frame portions, are captured such as, for example, the focus parameter or the like. Typically, the picture taking device 12 comprises an integrated display such as, for example, an LCD display on the backside of the digital camera.

A user of the intra-oral camera can see a picture of a tooth of a patient via the display device 14. Also, certain software analysis functions can be deployed to provide, for example, color shade analysis. Such captured parameters can, as well, be displayed on the display device. It is provided, in accordance with the present invention, that what is shown in the display device 14 is that which can be seen at that instance in the viewfinder of the camera—that is, that which would be captured in a picture taken by the camera at that instant. In lieu of the digital LCD display of a camera, a computer monitor can also be used which is coupled with a camera such that display information can be transmitted to the computer monitor.

The storage component 16 of the present invention stores, typically, the picture and, additionally, certain picture parameters. For example, color shade information such as, for example, certain color properties of tooth color shades, in accordance with a suitable color shade scheme table, are stored. Additionally, the storage element 16 serves as a buffer. The storage element 16 can be a semiconductor storage or a fixed plate or another suitable storage element such as, for example, a storage element in a computer. It is also possible, apart from the storage of a picture, to use a separate storage element, whereby it is possible to accomplish such storage via media such as a CD or a DVD.

Conventional elements can be deployed to serve as the user interface 18. In this connection, a keyboard, a mouse, a voice recognition system, and the like can be deployed. The user interface 18 permits a user to manipulate the picture taking device 12 in a suitable manner to thereby, for example, take a picture, to select a picture to be deleted, to determine the respective tooth a picture of which is to be taken, or the like.

The processing device 22 is typically a microprocessor or a microcomputer whose software operates for analyzing and identifying teeth color shades and which is available to provide the necessary functions for the taking of a picture. The required elements capable of performing such functions are conventionally available as circuits or, as well, as software. For example, a computer such as a personal computer (PC) can be provided to operate as the processing device 12, whereby it is to be understood that it is also possible to use elements which are conventionally comprised in a personal computer such as storage elements, displays, user interfaces, and communication devices as well as transmission devices to at least partially fulfill the operations of the display device 14, the user interface 18, the storage element 16, the communication device 20, and the output device 24. Separate processors or, as well, combinations of various processors, which are, in part, integrated into the camera and, in part, integrated into the personal computer, can be deployed.

In accordance with the present invention, a device for setting the camera into a proper picture taking position 26 is provided. The device for setting the camera into a proper picture taking position 26 supports the user with respect to the orientation of the picture taking device 22. Several components in the system 10 can be provided in this connection. Such components may comprise a pinpoint light source such as, for example, a laser diode, or a sharp focused light diode. Additionally, the hardware and the software which evaluate the picture information of the light patch produced by the irradiation of the area of interest by the pinpoint light source can also be considered.

The intra-oral camera 10 can be a component of a device for performing a color shade analysis. Such color shade analysis devices are described, for example, in U.S. Pat. No. 6,305,933 B1 and in WO 00/25696, whereby both of these references are fully incorporated by reference herein. It is preferred that a short tube for protection against false light is provided so that the picture that is taken is not contaminated by such false light. A tube of this type is shown, for example,, in U.S. Pat. No. 6,210,159 which is hereby fully incorporated by reference herein.

Figure 2:
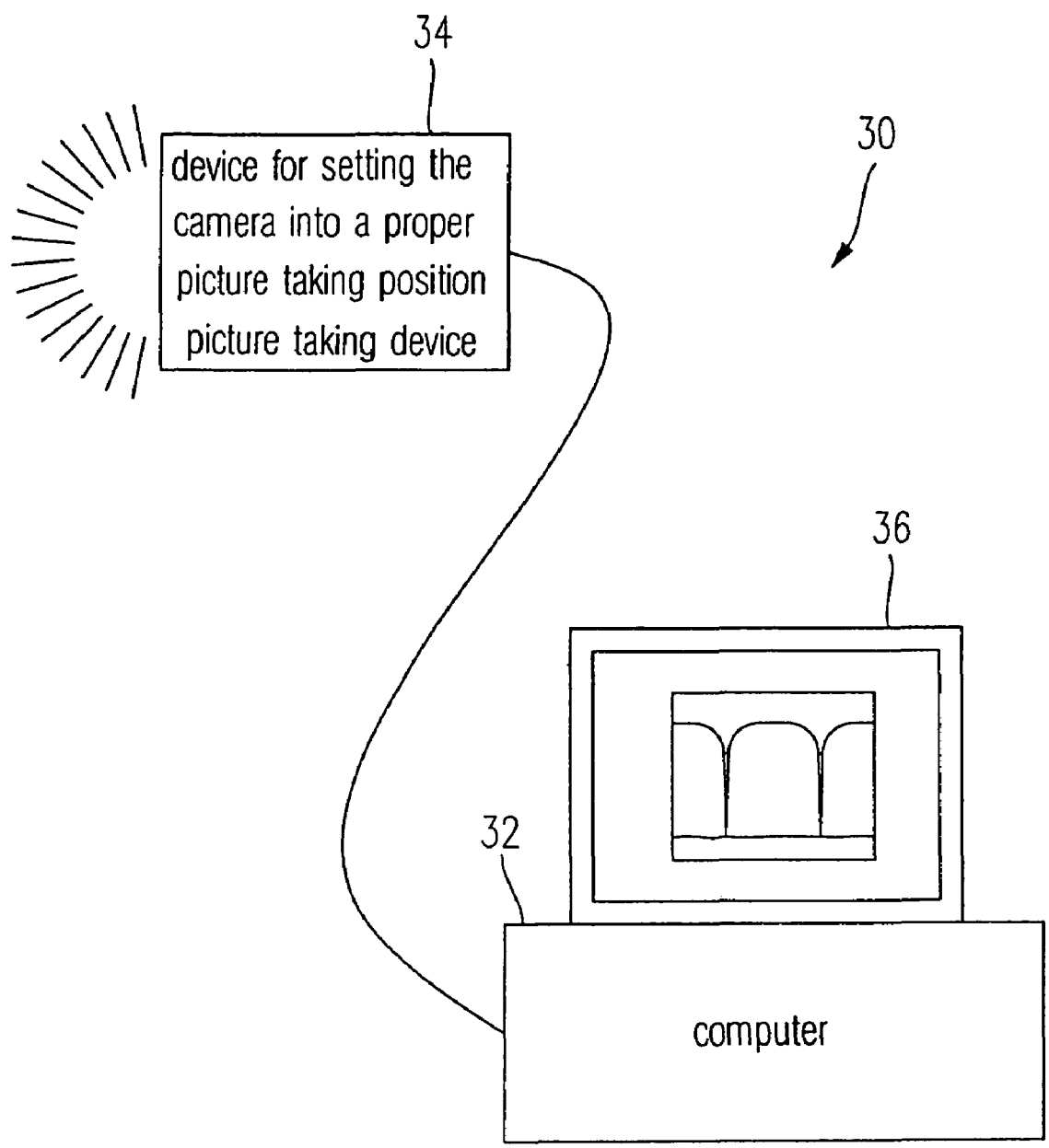
FIG. 2 is a functional block diagram of the intra-oral camera shown in FIG. 1 associated with a personal computer (PC)

An example of an intra-oral camera can be seen in FIG. 2, whereby, at the same time, the connection with a PC is illustrated. In connection with the intra-oral camera 30, it can be seen that the target alignment is completed and a picture of the tooth of a patient can be taken. An intra-oral camera comprises a PC 32 and a combination alignment setting and picture taking device 34. In a conventional manner, the PC 32 is communicated with a computer monitor 36 which operates as a display device. The combination alignment setting and picture taking device 34 captures the color and shape information relating to the tooth of a patient. The computer monitor 36 displays the picture which the picture taking device has just captured—that is, the picture of the object of interest which can be seen at that instant through the viewfinder of the camera. Depending upon the respective adjustment setting, a stored picture can be displayed as well on the monitor. At the same time, an analysis of the picture can be undertaken via the PC 32 and/or via the hardware of the combination alignment setting and picture taking device 34.

Analyses can be performed in order to determine whether the combination alignment setting and picture taking device 34 is properly aimed toward the object of interest. As desired, other functions can be performed as well such as, for example, an identification of the color shade with reference to a color shade reference table. In accordance with the present invention, the combination alignment setting and picture taking device 34 includes, for supporting the user's picture taking task, a picture taking alignment device for properly orienting the intra-oral camera in its operating position. In this regard, the picture taking alignment device for properly orienting the intra-oral camera in its operating position assures that the combination alignment setting and picture taking device 34 is properly aimed.

Figure 3:
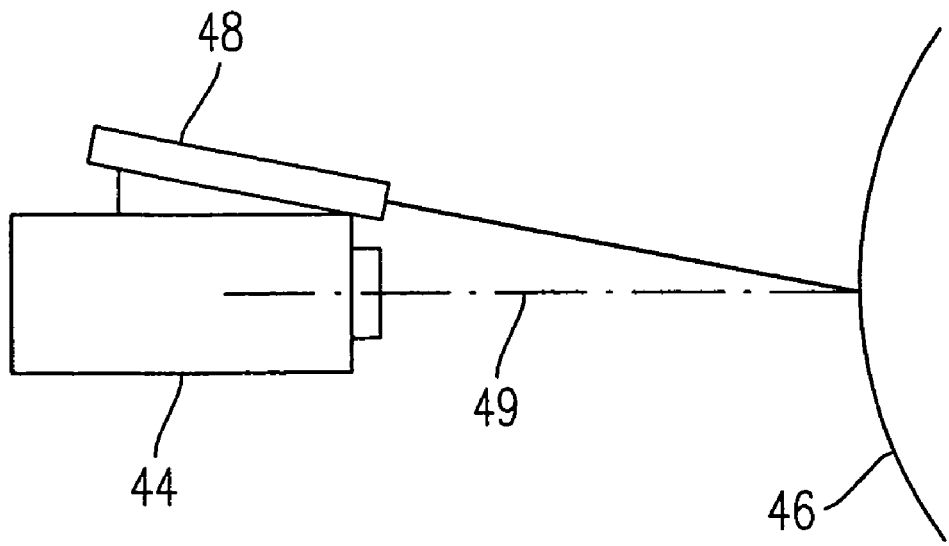
FIG. 3 is a schematic side elevational view of the one embodiment of the intra-oral camera of the present invention shown in FIGS. 1 and 2 and showing, in its position relative to a surface of a tooth, the picture taking alignment device for properly orienting the intra-oral camera in its operating position for orienting the intra-oral camera for taking a picture of the surface of the tooth.
Figure 4:
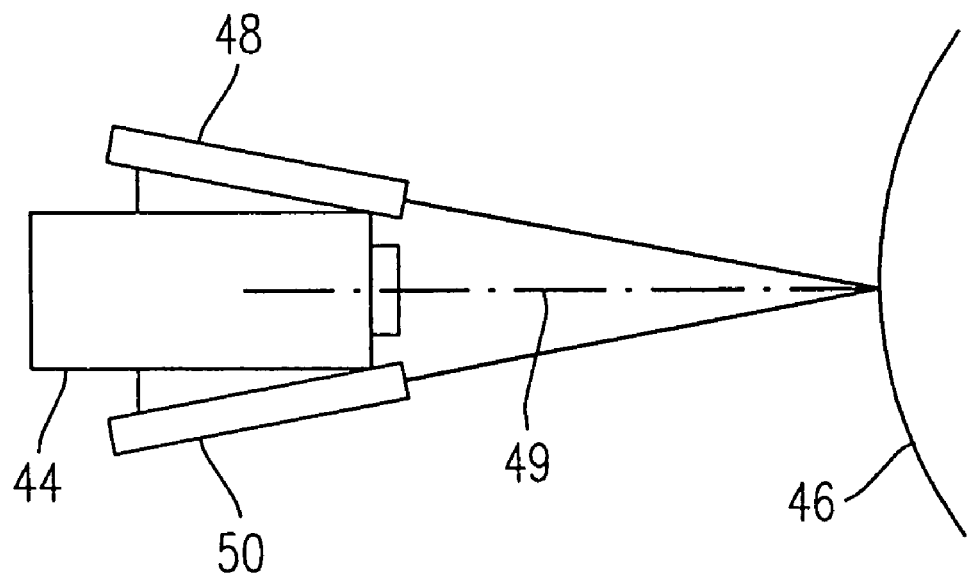
FIG. 4 is a schematic side elevational view of another embodiment of the intra-oral camera of the present invention, and showing, in their respective positions relative to a surface of a tooth, the picture taking alignment device for properly orienting the intra-oral camera in its operating position for orienting the intra-oral camera for taking a picture of the surface of the tooth and a picture sharpening adjustment device, both such devices being oriented toward the surface of the tooth.

FIGS. 3 and 4 schematically illustrate suitable picture taking and aiming devices. Typically, the correct aiming alignment is dependent upon the angle at which the camera is aimed toward the object a picture of which is to taken. In accordance with the present invention, the actual camera angle is analyzed in order to determine whether the relevant angle is correct or not. In FIGS. 3 and 4, cameras 44 are each aimed at a respective surface 46. The tooth surface 46 is typically convex, whereby, solely for the purposes of facilitating the description thereof herein, the proportions thereof are shown in an exaggerated manner. An incisor tooth comprises, for example, in its middle region, a planar but, nonetheless, structural surface that curves toward the side flanks—that is, the surface curves in the mesial or distal directions. In the event of an aiming error, a camera would record various color shades of the object of interest so that the restoration result based upon such color shades would not faithfully duplicate the respective dental structure comprising the object of interest. In order to prevent this occurrence, it is provided, in connection with the present invention, that the device for setting the camera into a proper picture taking position 26 (FIG. 1) is deployed.

In this connection, as seen in FIGS. 3 and 4, the pinpoint light source 48 is aimed toward the tooth surface 46. The pinpoint light source 48 is mounted, in the illustrated embodiment, on the camera 44 and, in fact, is so mounted that it is closely adjacent the optical axis 49 but is, however, spaced therefrom.

The light source 48 is mounted on the camera at a slight angle of, for example, 1 through 10° relative to the optical axis 49. To compensate for this divergence, the orientation is selected such that, at a given or predetermined spacing between the camera 44 and the tooth surface 46, the optical axis 49 and the light point produced via the light source 48 coincide at an intersection point. It is to be understood that, in this connection, a spacing determination is effected as well which, at the same time, facilitates the focusing of the picture taking device 12 in the camera 44.

In order to, as well, make visually clear for a user, such as, for example, a dentist, the focus operation of this type and, therefore, the establishment of the spacing, it is provided, as can be seen in FIG. 4, that two light sources 48 and 50 are operated together. The light points of both light sources 48 and 50 coincide upon achieving the proper spacing selection, in connection with which the optical axis 49 contemporaneously intersects the double light points and, preferably, intersects the double light points centrally thereof.

It is also possible to use a short tube or another suitable distance retainer which thereafter maintains the spacing following the initial setting thereof. Also, it is possible to undertake a measurement of the lightness via the camera 44, whereupon such a measurement measures the lightness of the produced light point and indicates, upon measuring a maximum lightness value, that the aiming orientation is being performed.

FIG. 4 illustrates that both light sources 48 and 50 are arranged at the same angle relative to the camera, with the respective angles being mirror-symmetrical to one another. It is to be understood that, in lieu of this, any other suitable desired number of suitable light sources can be arranged in a distribution pattern around the camera such as, for example, an annular distribution.

Figure 5:
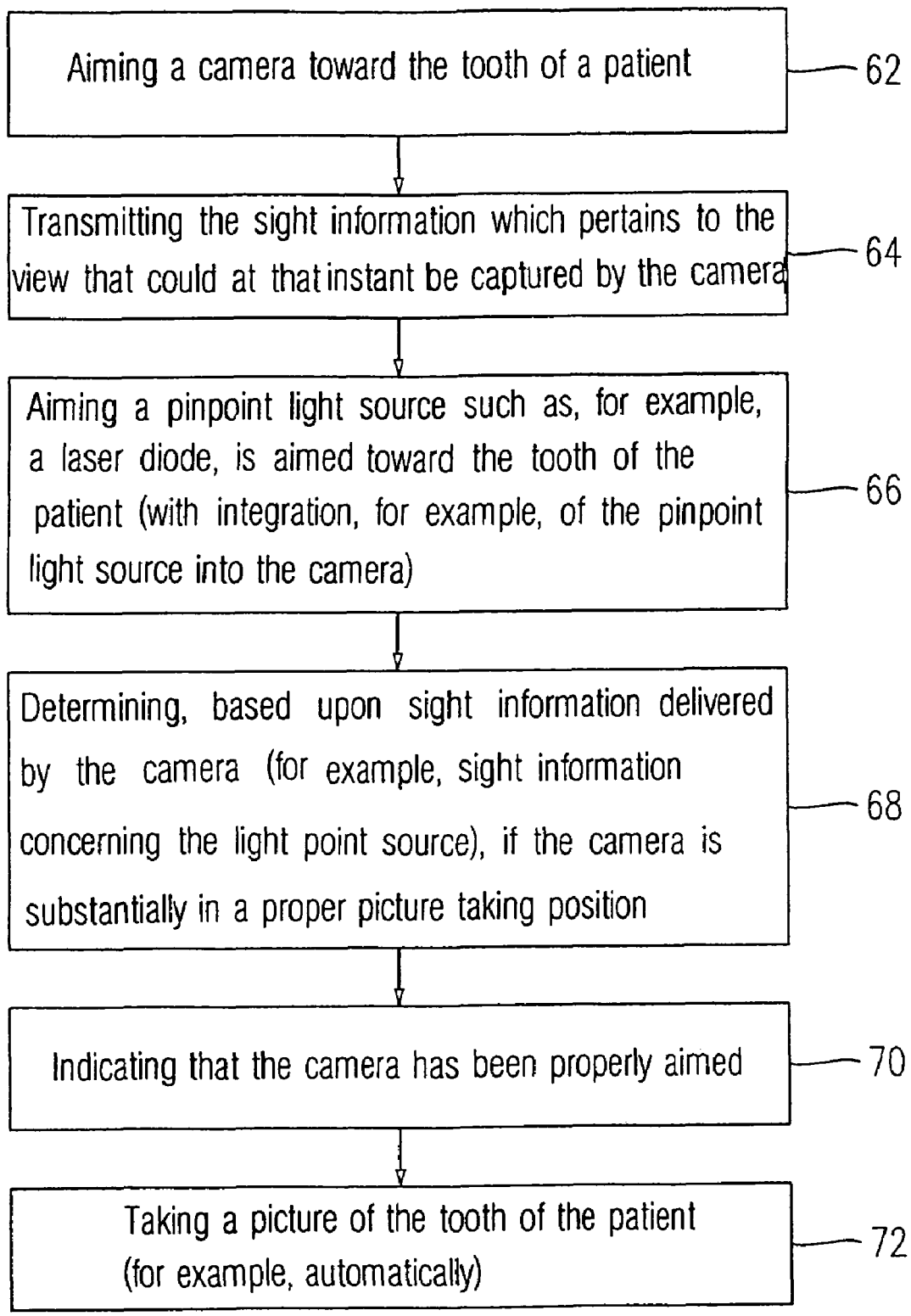
FIG. 5 is a flow diagram of the steps which a computer controlled picture taking alignment device for properly orienting the intra-oral camera performs to properly orient the intra-oral camera in accordance with the present invention.

FIG. 5 shows a schematic view in the form of a flow diagram which displays the inventive steps of the method of the present invention. In accordance with the function block 62, a camera is aimed toward the tooth of a patient in order to take a picture of the tooth. In accordance with step 64, the sight information is transmitted which pertains to the view that could at that instance be captured by the camera. According to step 66, a pinpoint light source such as, for example, a laser diode, is aimed toward the tooth of the patient and the light source is, for example, the integrated light source 48 or 50 illustrated in FIGS. 3 and 4. It is to be understood that, in lieu of such an arrangement, the basic principle can also be implemented by an external light source directed toward the tooth of the patient.

In accordance with step 68, a picture taking alignment device for properly orienting the intra-oral camera in its operating position 26 is provided if the camera is to be substantially properly aimed.

As can be seen in step 70 illustrated in FIG. 5, a display is provided indicating whether the camera has been properly aimed or not. In this regard, an audible or visual display device can be provided, for example, which indicates to the user that the camera is properly aimed. As is illustrated in step 72 of the flow diagram, a picture of the tooth of the patient is taken, for example, automatically, if the step illustrated in step 70 has shown that a predetermined interval has passed during which the indicator indicating the camera has been properly aimed has been actuated.

Of these steps, the steps 62 and 66 are typically performed by the user, while the steps 64, 68, 70, and 72 are, in the preferred embodiment of the invention, automatically performed—that is, are computer-controlled steps.

The aiming is preferably performed such that a limited selectively cropped camera frame portion of the captured picture is evaluated. This is shown in individual detail in FIG. 6. In step 82, it is determined that the picture taking device is aimed at a predetermined object of interest—that is, typically, aimed at the tooth a picture of which is to be taken. The picture information is then captured—and retained in step 84, whereby a predetermined or preselected selectively cropped camera frame portion is established which illustrates a small portion of the entire picture. The surface of the respective selectively cropped camera frame portion can comprise, for example, less than 10% and, in particular, less than 1%, of the entire picture.

The size of the selectively cropped camera frame portion is dependent upon the light patch and its size and configuration, that is, the light patch being produced by the light sources 48 and 50 on the tooth. In accordance with the present invention, it is, in any event, provided that the selectively cropped camera frame portion captures the entire light patch.

In an advantageous embodiment of the present invention, the selectively cropped camera frame portion is now partitioned into subdivisions which are explained in more detail with reference to FIG. 7.

In lieu of the decidedly cost favorable laser diode, it is also possible to deploy a laser which can produce a sharply limited light patch or light point. A laser is, however, substantially more expensive and brings with it only a certain limited value so that the cost favorable light sources are, in contrast, preferable.

As is clearly indicated in step 86, the picture information of the selectively cropped camera frame portion is evaluated in order to determine whether the camera is properly aimed at the object of interest. For example, picture information relating to the color, the shape, and the lightness of the light point produced by the pinpoint light source can be evaluated in order to determine if proper aiming has been accomplished.

Figure 6:
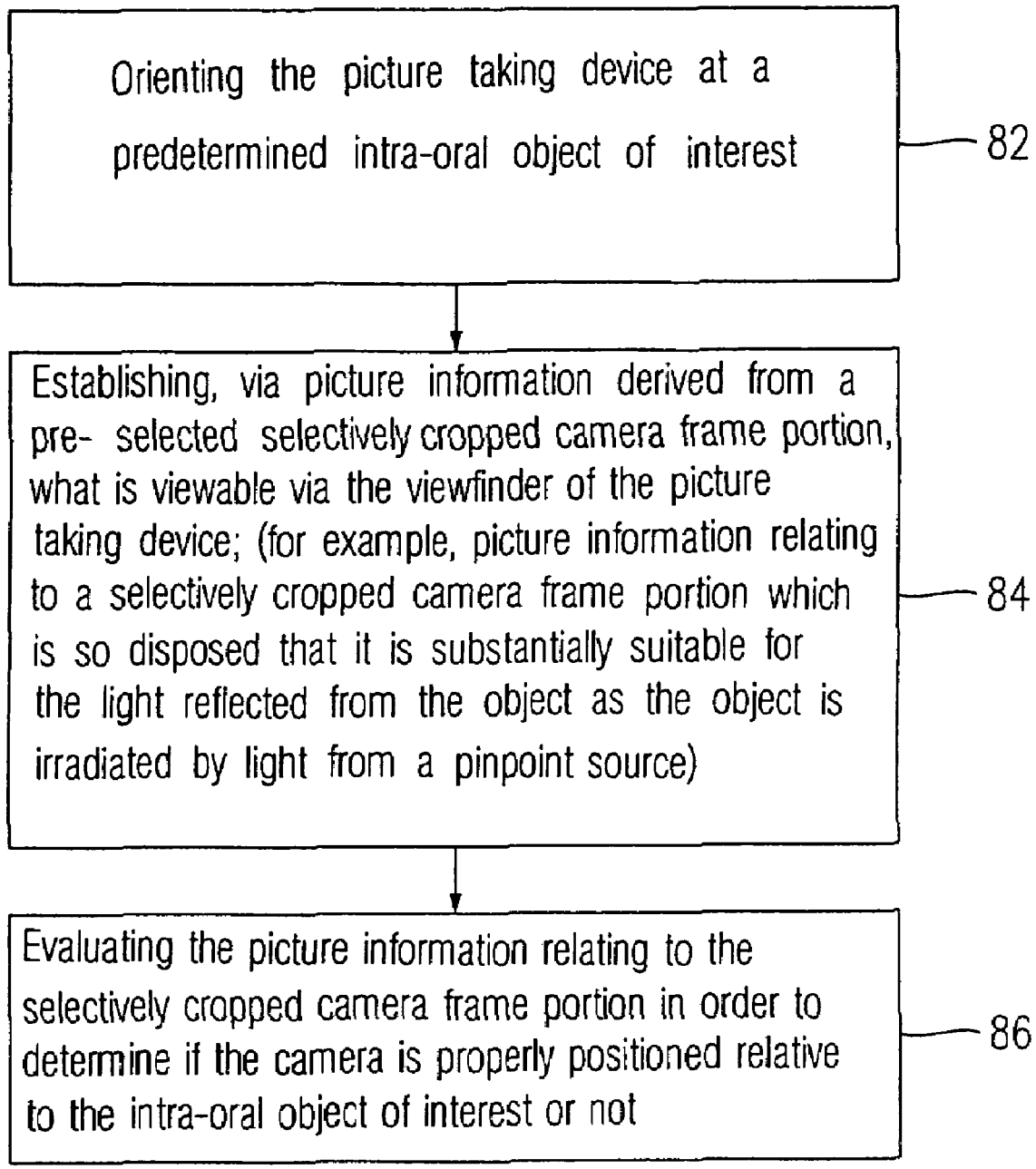
FIG. 6 is a flow diagram of the steps by which an evaluation of the proposed orientation of the intra-oral camera is performed by a respective embodiment of the present invention.

In the steps illustrated in FIG. 6, the steps 84 and 86 are typically steps which are performed by the computer, while step 82 is performed by the user.

Figure 7:
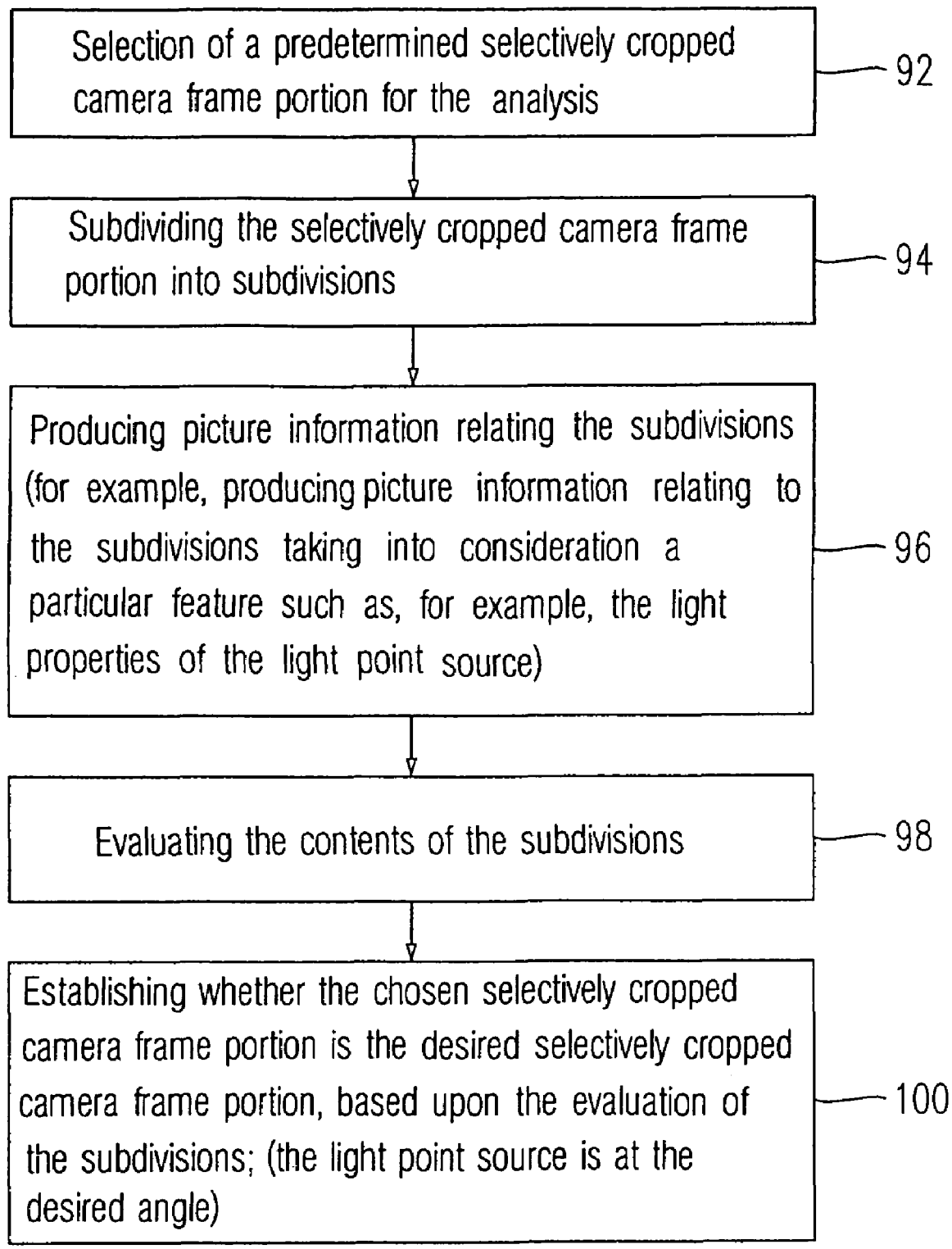
FIG. 7 is a flow diagram of the steps by which an identification of a suitable selectively cropped camera frame portion is performed by a further embodiment of the present invention.
Figure 8:
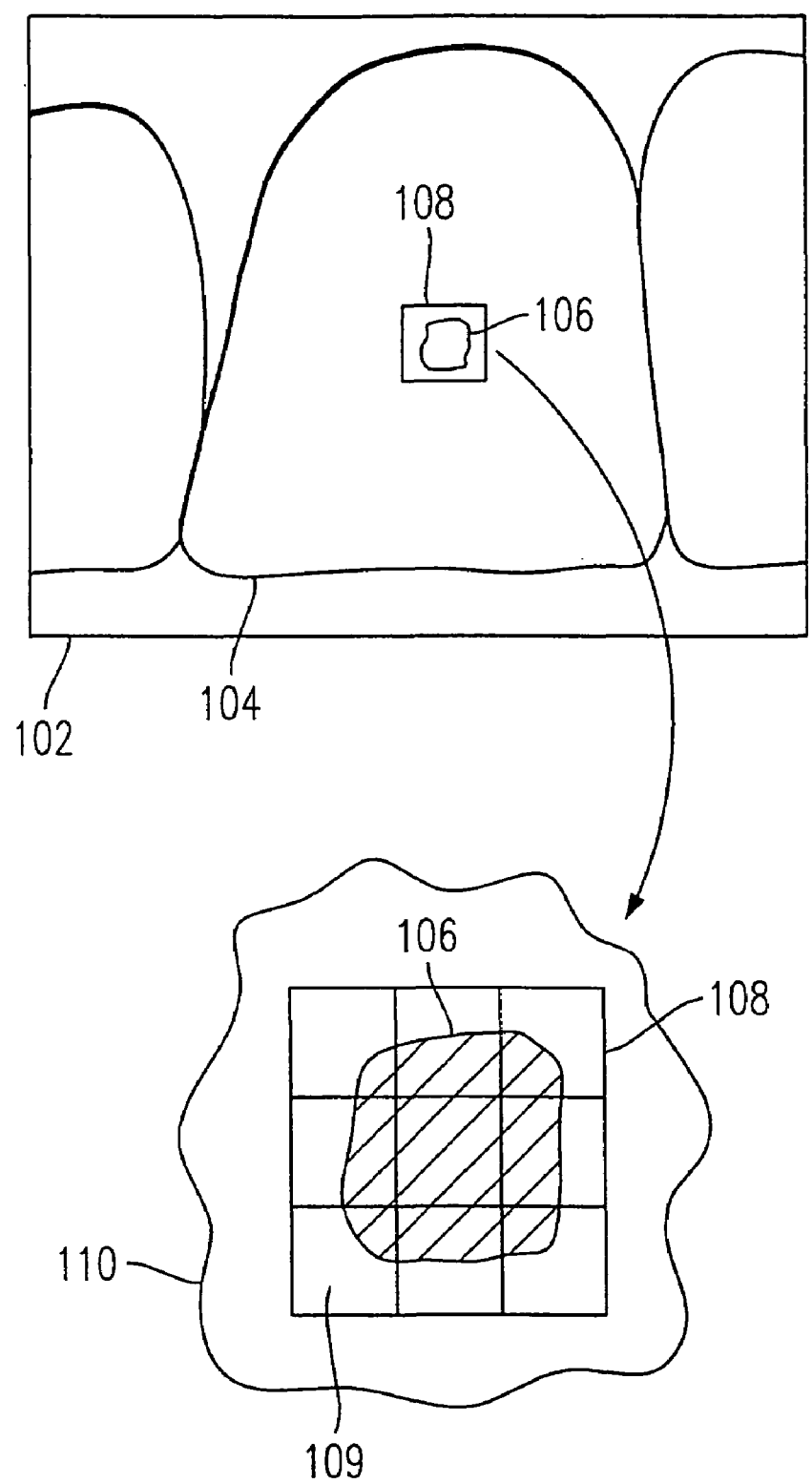
FIG. 8 is an enlarged front plan view of a camera picture and showing a selectively cropped camera frame portion of such camera picture which is used in connection with evaluating a proposed orientation of the intra-oral camera in accordance with the present invention.

FIG. 7 illustrates the manner in which the picture information is evaluated. In an advantageous embodiment, a grating of 3×3 grating fields is produced, as is also illustrated in FIG. 8. In that there is a selection [step 92] of a predetermined selectively cropped camera frame portion for the analysis, the selectively cropped camera frame portion is then, in step 94, partitioned into subdivision. The partitioning can be automatically performed at this step but, however, as the occasion arises, can also be performed by the user via a justification operation. Preferably, each subdivision contains the same number of pixels such as, for example, 20 pixels, whereby it is to be understood that any suitable desired subdivision arrangement can be set up.

In accordance with step 96, the picture information of the subdivisions is now captured. In this connection, the light parameter of each subdivision is captured, this information then being compared, in step 98, to that of the other subdivisions. According to step 100, it is then determined whether one of these subdivisions is the desired selectively cropped camera frame portion which displays the middle of the tooth.

Also, if the inventive method is deployed with respect to capturing a picture of a complete tooth, it is to be understood, that, in lieu of this, a portion of a tooth can be captured as well and a corresponding evaluation of such can be undertaken.

To evaluate and identify the subdivisions, a comparison can be performed on, for example, the lightness properties of two subdivisions disposed opposite one another. The orientation is then determined as the middle orientation if the lightness values of these opposed two subdivisions agree with one another. This serves to provide the orientation evaluation function, then, so long as the light patch produced by the light sources 48 and 50 exhibits a symmetrical lightness distribution such as, for example, a distribution in accordance with a Gaussian curve.

It is also possible to compare the absolute lightness value of the central subdivision with the lightness value of a relatively more remote subdivision. In a suitable different manner, the symmetry of the lightness can be evaluated, whereby, as well, information can also be captured to determine whether the horizontal-lateral and the vertical lateral subdivisions are each comprised of the same lightness.

FIG. 8 schematically illustrates the manner in which a camera view 102, which comprises a picture of a tooth 104, can be evaluated. Light from a pinpoint light source can be directed onto the tooth 104 in order to produce a light point 106 on the tooth 104. The raster [portion 108], is a selectively cropped camera frame portion which is selected to evaluate the light properties of the light produced on the tooth 104 by the irradiation thereof by the pinpoint light source.

As can be seen in the lower portion of FIG. 8, an enlargement of the selectively cropped camera frame portion 108 and of the light point 106 is illustrated. The raster [selectively cropped camera frame portion 108] is, in accordance with the present invention, subdivided into a plurality of fields [subdivisions 109]. This selectively cropped camera frame portion can be comprised of a configuration and size which is selected such that they are suitable for the typical form and size of the light point 106. An exact aiming is then achieved if the light point of the light source is located in the central field of the raster [selectively cropped camera frame portion 108]. It is to be understood, that typical camera spacings can be deployed and the size of the thus produced light point can be empirically transmitted. Examples of intra-oral camera systems are described in German Patent Publications P 101 20 717.4 and P 101 26 887.4, both of these references being fully incorporated by reference herein.

Figure 9:
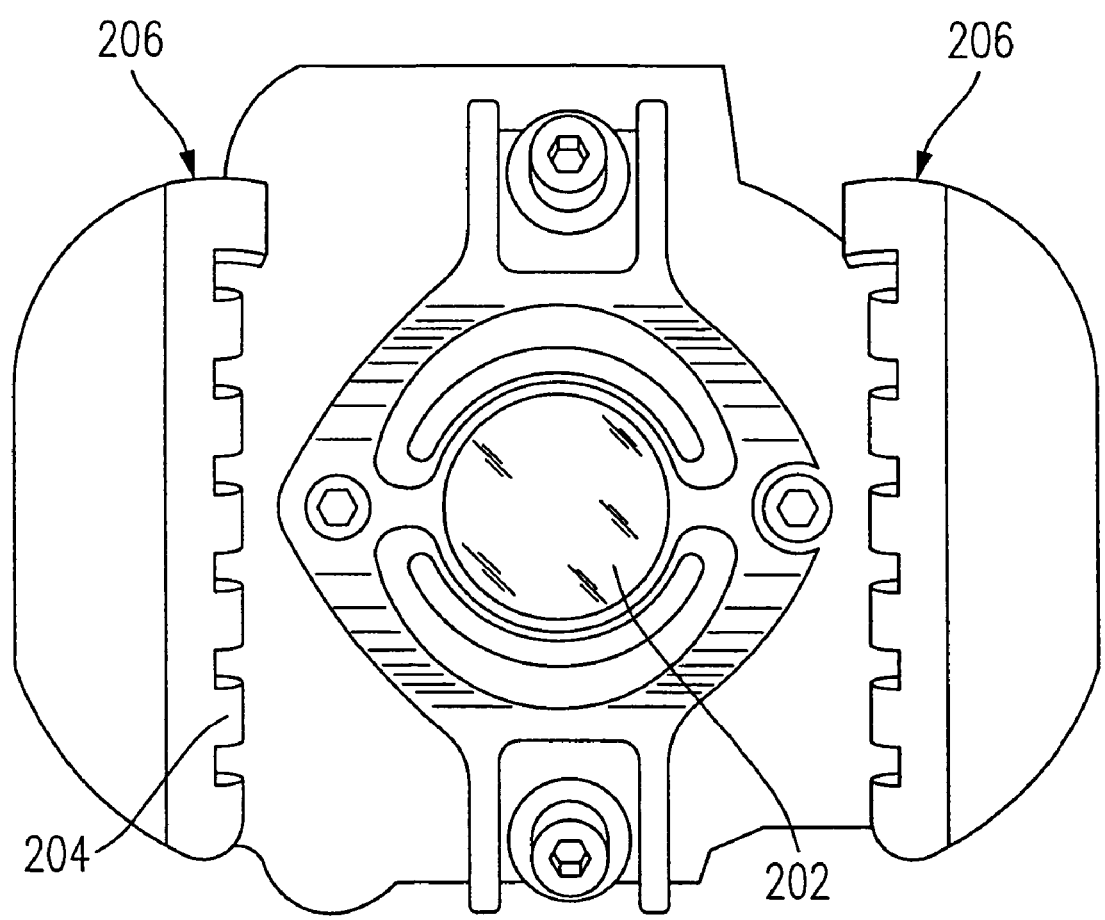
FIG. 9 is a front elevational view of an embodiment of the camera system of the present invention has laser diodes for assisting in orienting the intra-oral camera.
Figure 10:
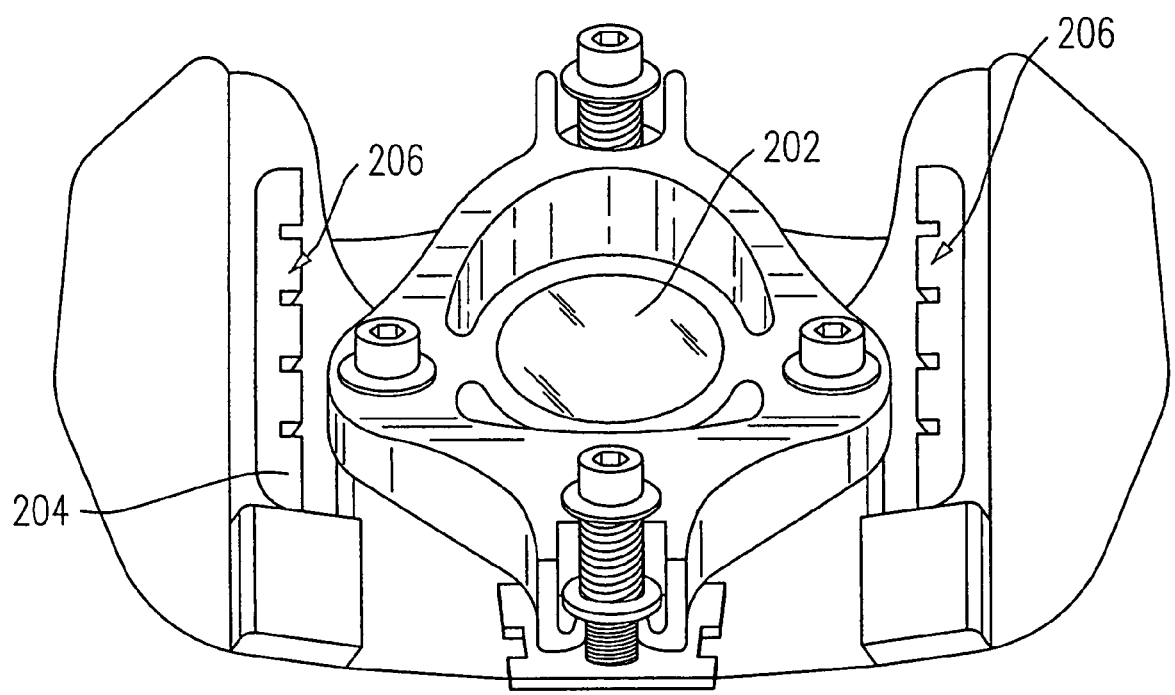
FIG. 10 is a top plan view of the embodiment of the camera system of the present invention shown in FIG. 9.
Figure 11:
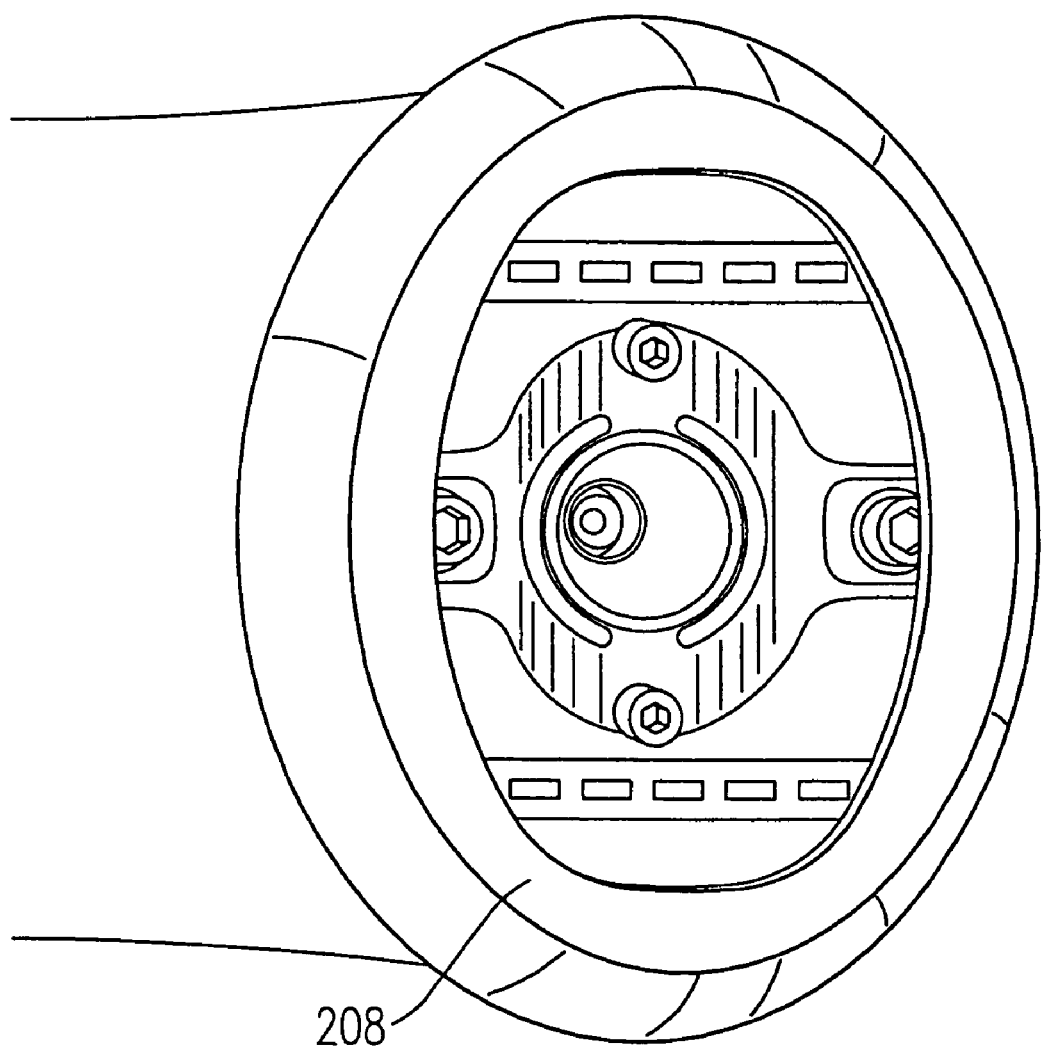
FIG. 11 is a perspective view of the embodiment of the camera system of the present invention shown in FIGS. 9 and 10 which further shows an inventive camera lens aperture configured with a short standoff tube.

FIGS. 9–11 illustrate a camera 200 in accordance with the present invention Each pinpoint light source 206 is, in this embodiment, configured via five laser diodes 204 arranged serially adjacent one another in a row, these laser diodes being laterally to the side of the objective or lens 202 of the camera. It is to be understood, that in lieu of this arrangement, an individual laser diode 204 can be deployed. FIG. 11 shows, additionally, a short standoff tube with a ring 208 that is configured for disposition on the patient or the tooth of the patient and which sets the spacing between the camera and the tooth. It is to be understood that a standoff ring of this type is not strictly required.

The present invention is, of course, in no way restricted to the specific disclosure of the specification and drawings, but also encompasses any modifications within the scope of the appended claims.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

The invention claimed is:

1. An intra-oral camera for producing a picture of an intra-oral object wherein the intra-oral object may include a tooth of a dental patient, the intra-oral camera comprising:
   a camera (44) operable to take a picture of the intra-oral object once the camera has been oriented in a proper picture taking position relative to the intra-oral object, the camera being operable to capture sight information relating to the intra-oral object;

a pinpoint light source for irradiating the intra-oral object with a pinpoint light beam, the pinpoint light source comprising at least one laser diode that projects a light point onto the tooth of the dental patient and the camera (44) provides sight information relating to the light properties of the light coming from the intra-oral object in response to the irradiation thereof by the light point projected on the intra-oral object by the laser diode; and indicating means (26) operable to evaluate sight information relating to the light property of one of the laser diodes and to indicate that the camera (44) has substantially assumed the proper picture taking position relative to the intra-oral object as soon as the camera has either been focused or has been properly aimed, the indicating means (26) being operable to subdivide a selected selectively cropped camera frame portion relating to the sight information into subdivisions and to evaluate a raster formed by such subdivisions by comparing the light properties of various fields of the raster and thereby determine whether the camera (44) has substantially assumed the proper picture taking position relative to the intra-oral object.

2. An intra-oral camera for producing a picture of an intra-oral object wherein the intra-oral object may include a tooth of a dental patient, the intra-oral camera comprising:

a camera (44) operable to take a picture of the intra-oral object once the camera has been oriented in a proper picture taking position relative to the intra-oral object, the camera being operable to capture sight information relating to the intra-oral object;

a pinpoint light source for irradiating the intra-oral object with a pinpoint light beam; and indicating means (26) for indicating that the camera (44) has substantially assumed the proper picture taking position relative to the intra-oral object for the taking of a picture of the intra-oral object, the indicating means (26) being operable to evaluate at least one of sight information relating to the intra-oral object and light, captured by the camera (44), which comprises light coming from the intra-oral object in response to the irradiation thereof by the pinpoint light source and to provide an indication that the camera (44) has substantially assumed the proper picture taking position relative to the intra-oral object based upon such evaluation, wherein the indicating means (26) is operable to subdivide a selected selectively cropped camera frame portion relating to the sight information into subdivisions, wherein the selectively cropped frame portion is at least 10 times smaller than the sight information and the indicating means (26) is operable to subdivide the selected selectively cropped camera frame portion into a point symmetric number of subdivided fields collectively forming a raster mass and the indicating means (26) is operable to evaluate the raster mass by capturing and comparing with one another at least one of parameters and light properties of the various adjacent ones of the fields of the raster mass and to thereby determine whether the camera (44) has substantially assumed the proper picture taking position relative to the intra-oral object.

3. A method for producing a picture of an intra-oral object wherein the intra-oral object may include a tooth of a dental patient, the method comprising:

providing an intra-oral camera and a pinpoint light source;

orienting the camera (44) to take a picture of the intra-oral object, the camera being operable to capture sight information relating to the intra-oral object;

optionally as needed, adjusting the orientation of the pinpoint light source relative to the intra-oral object such that the intra-oral object will be irradiated by a light beam from the pinpoint light source as the camera (44) is actuated to take a picture of the intra-oral object; and indicating, in response to an evaluation of at least one of sight information relating to the intra-oral object and light, captured by the camera (44), which comprises light coming from the intra-oral object in response to the irradiation thereof by the pinpoint light source, that the camera (44) has substantially assumed a proper picture taking position relative to the intra-oral object for the taking of a picture of the intra-oral object and further comprising:

subdividing a selected selectively cropped camera frame portion relating to the sight information into subdivisions, wherein the subdivisions form the fields of a raster, thereafter indicating that the camera (44) has generally assumed a proper picture taking position relative to the intra-oral object, thereafter comparing with one another the light properties of the various fields of the raster, and thereafter indicating, via marking of the central fields of the raster, that the camera (44) has substantially assumed the proper picture taking position relative to the intra-oral object.

* * * * *